//  
United States Patent [19]

Dominy

[11] 4,069,827
[45] Jan. 24, 1978

[54] DIATHERMY APPARATUS

[75] Inventor: Francis I. Dominy, Janesville, Wis.

[73] Assignee: The Burdick Corporation, Milton, Wis.

[21] Appl. No.: 605,988

[22] Filed: Aug. 20, 1975

[51] Int. Cl.² .............................................. A61N 1/40
[52] U.S. Cl. .................................................. 128/422
[58] Field of Search ................ 128/404, 405, 413, 422

[56] References Cited

U.S. PATENT DOCUMENTS

| | | | |
|---|---|---|---|
| 2,415,799 | 2/1947 | Rigfel et al. | 128/422 |
| 2,752,496 | 6/1956 | Martens | 128/422 |
| 3,127,895 | 4/1964 | Kendall et al. | 128/422 |
| 3,543,762 | 12/1970 | Kendall | 128/422 |
| 3,566,877 | 3/1971 | Smith et al. | 128/422 |

*Primary Examiner*—William E. Kamm
*Attorney, Agent, or Firm*—Mason, Kolehmainen, Rathburn & Wyss

[57] ABSTRACT

A diathermy apparatus includes a power oscillator for developing signals which are coupled to a patient by a tuned reactive coupling circuit. The magnitude of the oscillator signal is detected in the oscillator output circuit, and a corresponding control signal is developed. A reference signal is supplied by an output level selection circuit. The load imposed by the patient and the output circuit upon the power oscillator, and thus the magnitude of the oscillator signal, are maintained substantially constant by a servo control circuit. A motor driven variable impedance in the reactive coupling circuit is operated in response to differences between the control and reference signals.

8 Claims, 1 Drawing Figure

U.S. Patent  Jan. 24, 1978  4,069,827
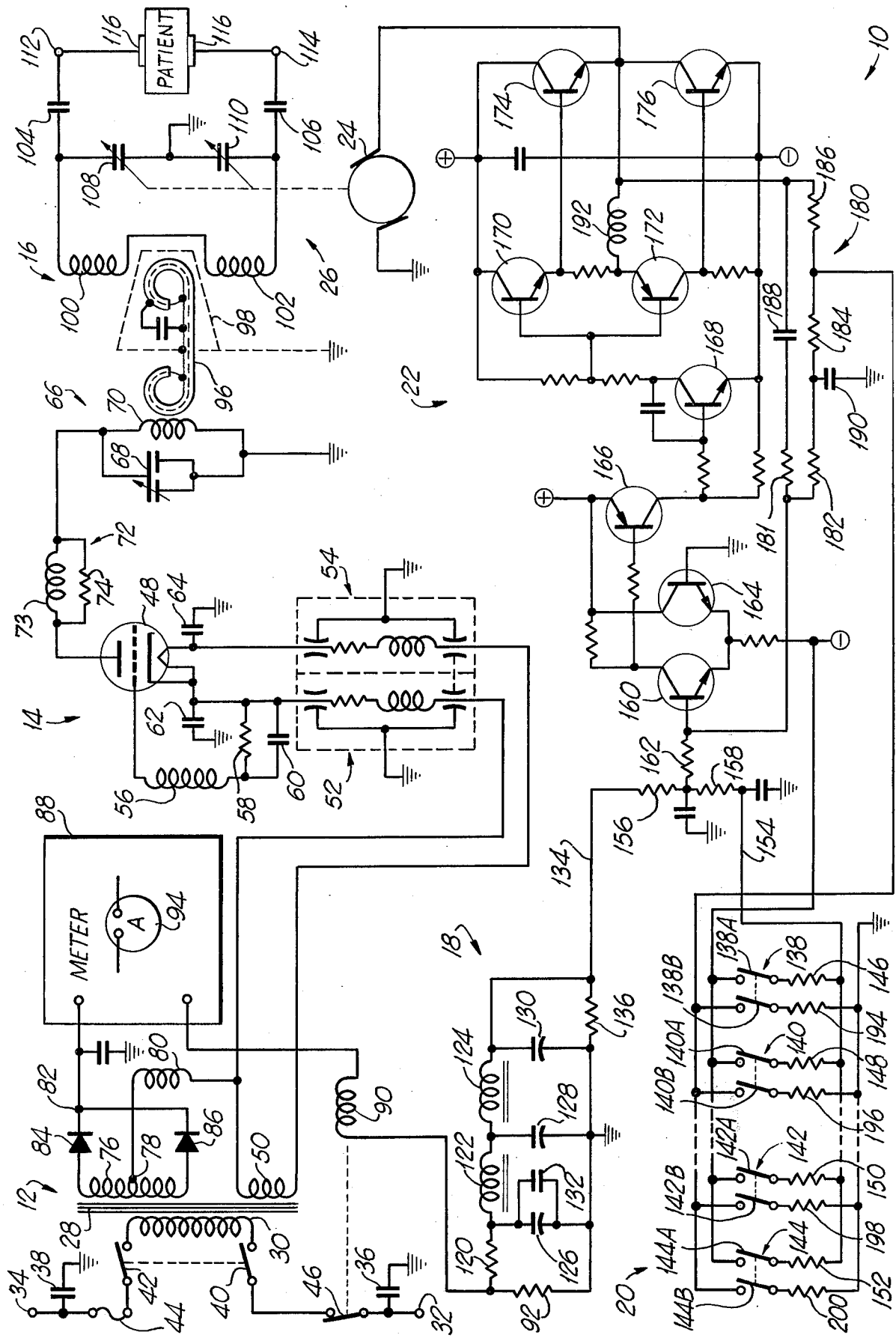

DIATHERMY APPARATUS

The present invention relates to diathermy apparatus and more particularly to a self-tuning diathermy apparatus.

The application of heat to various parts of a patient's body has been found to be beneficial in many instances. The term diathermy is used to describe the heating produced in body tissues as a result of the application of high frequency electrical currents. Two types of diathermy apparatus are currently widely used, these being shortwave diathermy apparatus operating at a frequency of, for example approximately 27 Mhz., and microwave diathermy apparatus operating at a substantially higher frequency of, for example, approximately 2450 Mhz.

A typical shortwave diathermy apparatus of a type used in the past includes a power oscillator developing an oscillator signal at the desired frequency. Electrical energy is applied by means of a tuned reactive coupling circuit from the oscillator to the patient through the agency of suitable patient applicators or electrodes. The patient functions effectively as an impedance in the tuned coupling circuit, and the coupling of the apparatus to the patient, the positioning of the patient relative to the applicators or electrodes, and the impedance of the internal output circuit components of the apparatus determine the oscillation magnitude. In the use of such prior art devices, typically a meter is provided, and an operator of the device may manually tune the reactive coupling circuit in order to control the transfer of electrical energy to the patient. Difficulties encountered with this prior art arrangement include the inconvenience of manually tuning the device, as well as problems which can arise due to patient movement or other changing conditions after initial tuning.

In order to overcome such problems, it has been proposed to provide servo-amplifier controlled self-tuning of diathermy apparatus. Siemens-Reiniger-Werke AG of Erlangen, Germany has manufactured and sold a shortwave diathermy apparatus identified by the product designation "Ultratherm 603" including a self-tuning feature identified by the product designation "Servomat". This arrangement utilizes a motor-controlled tunable impedance in the reactive coupling circuit. The motor is operated continuously in alternate directions across a peak current level. A multivibrator circuit or flip-flop reverses the motor direction each time the current level moves through a peak point.

Among the important objects of the present invention are to provide improvements in diathermy apparatus and to provide improved self-tuning capabilities in shortwave diathermy apparatus.

In brief, in accordance with the above and other objects and advantages of the present invention there is provided a diathermy apparatus including a power oscillator adapted to be coupled to a patient by means of a reactive coupling circuit. Sensing means in the oscillator output circuit provides a control signal indicative of the magnitude of oscillations. An adjustable impedance is included in the reactive coupling circuit and is adjustable by means of a drive motor. An output level selecting circuit includes switching means for providing a reference signal corresponding to a desired output level. When the control signal varies from the reference signal, an amplifier provides a drive signal for operating the drive motor thereby to vary the impedance of the reactive coupling circuit until a null point is reached and the oscillation magnitude is at the desired level.

The invention together with its objects and advantages may be best understood from the following detailed description of a preferred embodiment of the invention illustrated in the accompanying drawing.

The single FIGURE of the drawing is a schematic and diagrammatic illustration of a diathermy apparatus constructed in accordance with the principles of the present invention.

With reference now to the drawing, there is illustrated a diathermy apparatus designated as a whole by the reference numeral 10 and constructed in accordance with the principles of the present invention. In general, the apparatus 10 includes an input or power supply circuit generally designated as 12 providing an operating potential for a power oscillator circuit generally designated as 14. Electrical energy is coupled from the power oscillator circuit 14 to a patient by means of a reactive coupling circuit generally designated as 16.

In accordance with an important feature of the present invention, the diathermy apparatus 10 is self-tuning in order to simplify use of the apparatus and to prevent undesirable variations in the tuning condition during use. A detecting and filtering circuit generally designated as 18 detects the magnitude of the oscillator output or load current. An output level selector circuit generally designated as 20 establishes a desired operating level. A servo-amplifier circuit generally designated as 22 operates a drive motor 24 to control a variable impedance means generally designated as 26 in the reactive coupling circuit 16 to maintain the oscillator output current at the desired level.

Proceeding now to a more detailed description of the components and operation of the diathermy apparatus 10, the input or power circuit 12 includes a power supply transformer 28 having a primary winding 30 coupled by means of a pair of power supply terminals 32 and 34 with a standard alternating current operating potential. A pair of bypass capacitors 36 and 38 provide radio frequency suppression, and a pair of ganged switches 40 and 42 provide for on-off control of the apparatus, for example by means of a suitable timer or the like (not shown). A fuse 44 protects the apparatus 10 in the usual manner, while overload protection contacts 46 guard against overload of the power oscillator 14 as described below.

The power oscillator circuit 14 includes a controlled conduction device in the form of a vacuum tube triode 48. Transformer 28 includes a secondary winding 50 for developing filament heating current for the triode 48. Winding 50 is connected to the filament of triode 48 by means of a pair of radio frequency filters 52 and 54.

Power oscillator circuit 14 is of the tuned plate - tuned grid configuration, and a self-resonant inductance 56 is coupled to the grid electrode of triode 48 for grid excitation. Grid bias is developed across a resistor 58 in parallel with a bypass capacitor 60. Capacitors 62 and 64 operate to bypass the filament heater circuit, while the radio frequency filters 52 and 54 provide the necessary decoupling from the power supply.

Frequency of operation of the oscillator circuit 14 is primarily determined by a tank circuit 66 including a capacitor 68 and an inductance 70. Capacitor 68 is variable so that the desired operating frequency of the diathermy apparatus 10 may be selected. A parasitic filter 72 including an inductance 73 and a resistor 74 is connected between the plate electrode of triode 48 and the tank circuit 66 for filtering high frequencies.

Operating potential for the power oscillator circuit 14 is provided by means of a secondary winding 76 of the transformer 28. A center tap terminal 78 of winding 76 serves as the relatively negative power supply terminal for the oscillator and is coupled to the cathode of triode 48 by means of a radio frequency isolation choke 80 and the radio frequency filter 52.

A relatively positive power supply terminal for the oscillator, designated by the reference numeral 82, is coupled to the winding 76 by a pair of diodes 84 and 86 providing full wave rectification. Relatively positive power supply terminal 82 is connected to a point of ground reference potential by means of a low impedance circuit including a meter generally designated as 88, a current sensing winding 90 controlling the overload protection contacts 46, and a current detection resistor 92 associated with the detecting and filtering circuit 18.

In view of the fact that both the resistor 92 and the tank circuit 66 are coupled to ground or reference potential, it can be seen that the main output or anode - cathode circuit of the oscillator triode 48 includes, in series connected relationship, the tank circuit 66, the filter 72, the anode and cathode of the triode 48, the radio frequency filter 52, the radio frequency choke 80, the halves of winding 76 and the rectifier diodes 84 and 86, the terminal 82, the meter 88, the winding 90, and the resistor 92. An ammeter 94 within the meter 88 provides a visible indication of the output level of the power oscillator circuit 14. Similarly, the current flowing in coil 90 is proportional to the output level of the triode 48. Winding 90 is arranged to operate contacts 46 to an open circuit condition should this current increase to a level which might be harmful to the triode 48.

A link coupler 96 of conventional configuration associated with a grounded faraday shield 98 serves to couple power oscillations from the tank circuit 66 to the reactive coupling circuit 16. Link 96, as will readily be understood by those skilled in the art, provides for efficient coupling while reducing harmonics and spurious energy transfer.

Coupling circuit 16 includes inductances 100 and 102, capacitors 104, 106, and variable capacitors 108 and 110 providing the necessary reactive tuning for energy transfer to a patient. A pair of output terminals 112 and 114 are adapted to be interconnected by means of patient applicators or electrodes 116 with a patient. The patient is effectively included as an impedance in the output circuit, i.e., in the reactive coupling circuit 16. The transfer of energy from the power oscillator circuit 14 to the coupling circuit 16 varies in accordance with the tuning of the circuit 16 accomplished in the illustrated arrangement by means of the variable impedance 26 comprising the two ganged variable capacitors 108 and 110. Movement of the patient during operation of the apparatus 10 varies the effective impedance of the circuit 16 and thus the coupling of energy between the oscillator circuit 14 and the reactive coupling circuit 16. Such changes are reflected in changes in the current flowing in the anode - cathode circuit of the power oscillator triode 48.

In accordance with an important feature of the present invention, the diathermy apparatus 10 is capable of self-tuning. Consequently, when operation is first initiated, the necessity for a manual tuning operation, as by manually adjusting the impedance of a variable impedance element in the coupling circuit 16, is avoided. Moreover, during operation of the diathermy apparatus 10, a desired tuning condition is automatically maintained by servo-controlled adjustment of the tuning condition of the coupling circuit 16 as required by changes in the effective impedance provided by the load or patient.

More specifically, in accordance with the present invention, the detecting and filtering circuit generally designated as 18 continuously develops a control signal indicative of the level of oscillations, - i.e., the magnitude of the output current present in the anode - cathode circuit of the oscillator triode 48. This control signal is continuously compared by means of the servo-amplifier circuit 22 with a reference signal provided by the output level selector circuit 20. When deviations occur between the control signal and the reference signal, amplifier 22 energizes motor 24 in order to adjust variable impedance means 26 in the proper direction to vary the tuning of the reactive coupling circuit 16 and thus the coupling of energy between the power oscillator circuit 14 and the circuit 16 in such a manner that the magnitude of oscillations is returned to the desired level.

More specifically, as indicated above current flowing in the anode - cathode circuit of triode 48 flows through resistor 92 to ground. In order to develop a control signal applied to amplifier 22, the voltage appearing across resistor 92 is filtered and attenuated. A filter consisting of resistor 120, inductances 122 and 124, and capacitors 126, 128 and 130 provides a low ripple signal by filtering power supply frequencies from the anode - cathode current. The resistor 120 together with a capacitor 132 also provide a radio frequency filter.

A circuit node 134 comprises the output of the detecting and filtering circuit 18 as well as a first input of the servo-amplifier circuit 22. Node 134 is connected with a point of ground or reference potential by means of a resistor 136 in order to load the detecting and filtering circuit 18 and to attenuate the control signal applied to the first input of the servo-amplifier circuit 22.

A reference signal for comparison with the control signal in the amplifier 22 is provided by the output level selector 20. This circuit includes a number of manually operated switches 138, 140, 142, 144, etc. As indicated by the broken lines in the circuit 20, any desired number of such manually operated switches may be included for selecting various desired reference signals. Each switch 138, 140, 142 and 144 includes first and second, ganged, normally open sets of switch contacts 138A and 138B; 140A and 140B; 142A and 142B; and 144A and 144B. Each of the "A" contacts is connected in circuit with a resistor 146, 148, 150 or 152 between a point of relatively negative supply potential and a circuit node 154. Node 154 comprises the output of the level selector circuit 20 and a second input of the amplifier circuit 22. The magnitudes of the resistors 146, 148, 150 and 152, as well as of other similar resistors associated with additional switches in the circuit 20, are chosen so that, upon closure of a selected switch, node 154 is supplied with a current of predetermined magnitude corresponding to a desired current at circuit node 134.

Servo-amplifier 22 compares the control and reference signals supplied by the circuits 18 and 20. More specifically, the control signal appears at the first amplifier input 134 while the reference signal appears at the second amplifier input 154. In a null condition when the oscillator output current is at the desired value, the amplifier input signal is zero because the current flowing to amplifier 22 at node 134 is balanced by, i.e., equal to, current flowing from the circuit 22 at the node 154. In this condition, the voltage appearing at the junction of a pair of resistors 156 and 158 is zero. Consequently, no operating bias is applied to a first stage input amplifier transistor 160 of the amplifier circuit 22.

In the event that the null condition changes, either due to operation of a different switch in the level selector circuit 20 or due to a change in the effective impedance of the reactive coupling circuit 16, a non-zero voltage appears at the junction of resistors 156 and 158. As a result, this voltage is coupled to the base electrode of transistor 160 through a resistor 162. A transistor 164 establishes the input operating point of the amplifier circuit 22, and transistors 166, 168 and transistors 170 and 172 provide additional stages of amplification. Transistors 170 and 172 operate as drivers for a pair of power output transistors 174 and 176 each connected in circuit with the motor 24 and either a point of relatively positive or of relatively negative supply potential.

In the operation of the servo-amplifier 22 and the variable impedance means 26, should the current flowing in the anode - cathode circuit of triode 48 increase or decrease relative to the desired magnitude established by operation of the circuit 20, the amplifier 22 will operate to render conductive either the transistor 174 or the transistor 176. As a result, the motor 24 will be operated in either of its alternate directions in order to adjust the impedance of the variable capacitors 108 and 110. This change in impedance adjusts the coupling between the power oscillator circuit 14 and the reactive coupling circuit 16 thus changing the effective load on the triode 48 and its anode - cathode current. This operation continues until a null point is reached at which the oscillation magnitude is at the desired level.

In accordance with a feature of the invention, the amplifier circuit 22 is provided with a feedback network 180 including resistors 181, 182, 184 and 186 and capacitors 188 and 190. The circuit branch including resistor 181 and capacitor 188 serves as a high frequency filter while the network including resistors 182, 184 and 186 and capacitor 190 functions as a low frequency filter. The feedback network couples the emitters of transistors 170 and 172 by way of a radio frequency choke 192 to the base of transistor 160 and provides degenerative feedback for stability. The gain of the amplifier 22, in accordance with the invention, is related to the desired operating point of the diathermy apparatus 10 by means of the level selector circuit 20.

More specifically, each switch 138, 140, 142 and 144 is provided with the second set of switch contacts 138B, 140B, 142B and 144B. Each set of "B" contacts is connected in series with a resistor 194, 196, 198 and 200 between a point of ground or reference potential and the junction of resistors 184 and 186 in the feedback network. As a result, by choosing the proper values of the resistors 194, 196, 198 and 200, the gain of the amplifier circuit 22 may be controlled so that desired stability and sensitivity in relation to the operating level of the oscillator 14 are provided.

While the present invention has been described with reference to details of the illustrated embodiment, it should be understood that such details are not intended to limit the invention as defined in the following claims.

What is claimed and desired to be secured by Letters Patent of the United States is:

1. In a diathermy apparatus, the combination comprising:
    an oscillator including a controlled conduction device having a pair of output electrodes;
    a tank circuit connected in circuit with said device output electrodes;
    means for applying direct current to said controlled conduction device, said current applying means including means for sensing the magnitude of the direct current applied to said controlled conduction device and providing a control signal indicative of said current, said control signal being indicative of the magnitude of the oscillations provided by said oscillator;
    a pair of output terminals adapted to be coupled to a patient;
    a reactive coupling circuit for coupling electrical energy from said tank circuit to said output terminals;
    adjustable means for varying the tuning of said coupling circuit;
    an output level selecting circuit including means for providing a reference signal corresponding to a desired output level;
    and an output amplifier having an output connected to said adjustable means and inputs connected to both said sensing means and said selecting circuit for operating said adjustable means in response to variance of said control signal relative to said reference signal.

2. The combination of claim 1, further comprising feedback means in said amplifier, and said selecting circuit including gain adjusting means connected to said feedback means.

3. The combination of claim 1, said adjustable means including a variable reactance in said reactive coupling circuit.

4. The combination of claim 3, said adjustable means including a bidirectional electric motor drivingly coupled to said variable reactance.

5. The combination of claim 1, said selecting circuit including switch means for altering the magnitude of said reference signal.

6. The combination of claim 5, said switch means including means connected to said amplifier for adjusting amplifier gain in response to operation of said switch means.

7. A shortwave diathermy apparatus comprising in combination:
    an oscillator for developing an oscillator signal;
    means coupled to said oscillator for applying said oscillator signal to a patient;
    variable impedance means coupled to said oscillator for varying the tuning of said oscillator;
    means for applying direct current to said oscillator for energizing said oscillator;
    means for detecting the magnitude of the direct current applied to said oscillator; and
    servo means coupled between said detecting means and said variable impedance means for varying said tuning in response to changes in said magnitude of said direct current.

8. A diathermy apparatus for coupling electrical energy through an applicator to a patient, said apparatus comprising a generator for developing an electrical signal, means coupled between said generator and the applicator for applying the electrical signal from said generator to said applicator; variable means coupled to said applying means for altering the tuning of said applying means thereby varying the magnitude of said electrical signal; motor means for operating said variable means; means for applying a unidirectional energizing current to said generator; level determining means for providing a first control signal of predetermined magnitude; detecting means responsive to the magnitude of said unidirectional current for providing a second control signal having a magnitude corresponding to the magnitude of said unidirectional current; and comparing means for applying to said motor means a drive signal proportional to a difference between said first and second control signals.

* * * * *